US00PP31878P2

(12) United States Plant Patent
Danziger

(10) Patent No.: US PP31,878 P2
(45) Date of Patent: Jun. 16, 2020

(54) ***VERBENA HYBRIDA* PLANT NAMED 'DVERVNWHI'**

(50) Latin Name: *Verbena hybrida*
Varietal Denomination: DVERVNWHI

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 16/350,542

(22) Filed: Nov. 30, 2018

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 6/86; A01H 5/02
See application file for complete search history.

*Primary Examiner* — Keith O. Robinson
(74) *Attorney, Agent, or Firm* — Cassandra Bright

(57) ABSTRACT

A new and distinct *Verbena* cultivar named 'DVERVNWHI' is disclosed, characterized by early flowering, an abundance of white flowers, semi-trailing habit and tolerance to powdery mildew. The new variety is a Verbena, normally produced as an outdoor garden or container plant.

2 Drawing Sheets

Figure 1:
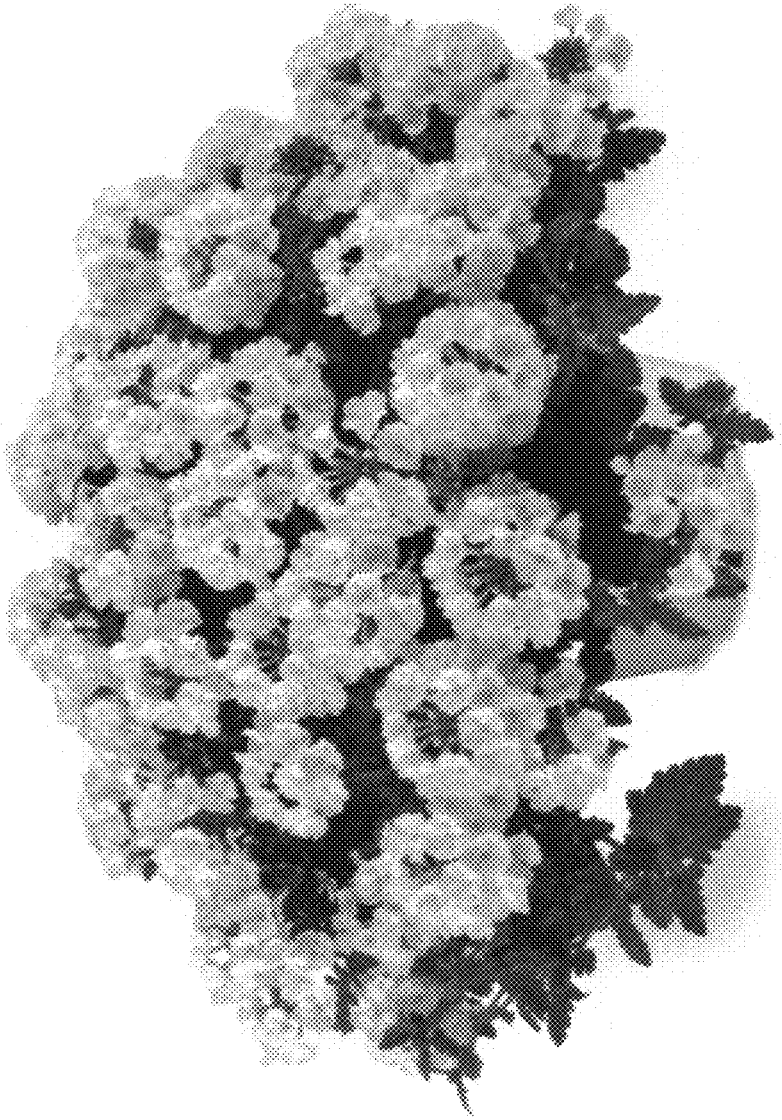

Latin name of the genus and species: *Verbena hybrida.*
Variety denomination: 'DVERVNWHI'.

BACKGROUND OF THE INVENTION

The new *Verbena* cultivar is a product of a planned breeding program conducted by the inventor, Gavriel Danziger in Moshav Mishmar Hashiva, Israel. The objective of the breeding program was to produce new *Verbena* varieties. The open pollination resulting in this new variety was made during May of 2014.

The seed parent is the, unpatented, propriety variety referred to as *Verbena* 'VE-14-7477'. The pollen parent is unidentified. The new variety was discovered in December of 2015 by the inventor in a group of seedlings resulting from the 2014 open-pollination, in a greenhouse in Moshav Mishmar Hashiva, Israel. Date of first sale was Dec. 3, 2017, in Belgium. This sale was made directly by the inventor or one who obtained the claimed invention directly or indirectly from the inventor. This sale and all public disclosures made before the filing of this application fall within the exception allowed under 102(b)(1).

Asexual reproduction of the new cultivar 'DVERVNWHI' by vegetative cuttings was first performed during December of 2015, at a greenhouse in Moshav Mishmar Hashiva, Israel. Subsequent propagation by vegetative cuttings has shown that the unique features of this cultivar are stable and reproduced true to type in multiple successive generations.

SUMMARY OF THE INVENTION

The cultivar 'DVERVNWHI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DVERVNWHI'. These characteristics in combination distinguish 'DVERVNWHI' as a new and distinct *Verbena* cultivar:

1. Flowers early.
2. Semi-trailing habit.
3. Tolerant to powdery mildew.
4. Highly floriferous plants—abundance of white flowers.

PARENT COMPARISON

Plants of the new cultivar 'DVERVNWHI' are similar to plants of the seed parent, *Verbena* 'VE-14-7477' in most horticultural characteristics, however, plants of the new cultivar 'DVERVNWHI' differ in the following;

1. The new variety is more vigorous than the seed parent which has weaker growth habit.
2. The new variety is more floriferous than the seed parent.

COMMERCIAL COMPARISON

Plants of the new cultivar 'DVERVNWHI' can be compared to the unpatented commercial variety *Verbena* 'Estrella White Imp'. These varieties are similar in most horticultural characteristics; however, 'DVERVNWHI' differs in the following:

1. The new variety is more vigorous then the comparable variety.

Plants of the new cultivar 'DVERVNWHI' can also be compared to the unpatented commercial variety *Verbena* 'Lanai White'. These varieties are similar in most horticultural characteristics; however, 'DVERVNWHI' differs in the following:

1. The new variety has a cup shape flower, while the comparable variety has flat shape flower.

BRIEF DESCRIPTION OF THE PHOTOGRAPHS

The accompanying photograph in FIG. 1 illustrates in full color a typical plant of 'DVERVNWHI' grown in in a greenhouse, in Moshav Mishmar Hashiva, Israel.

Figure 2:
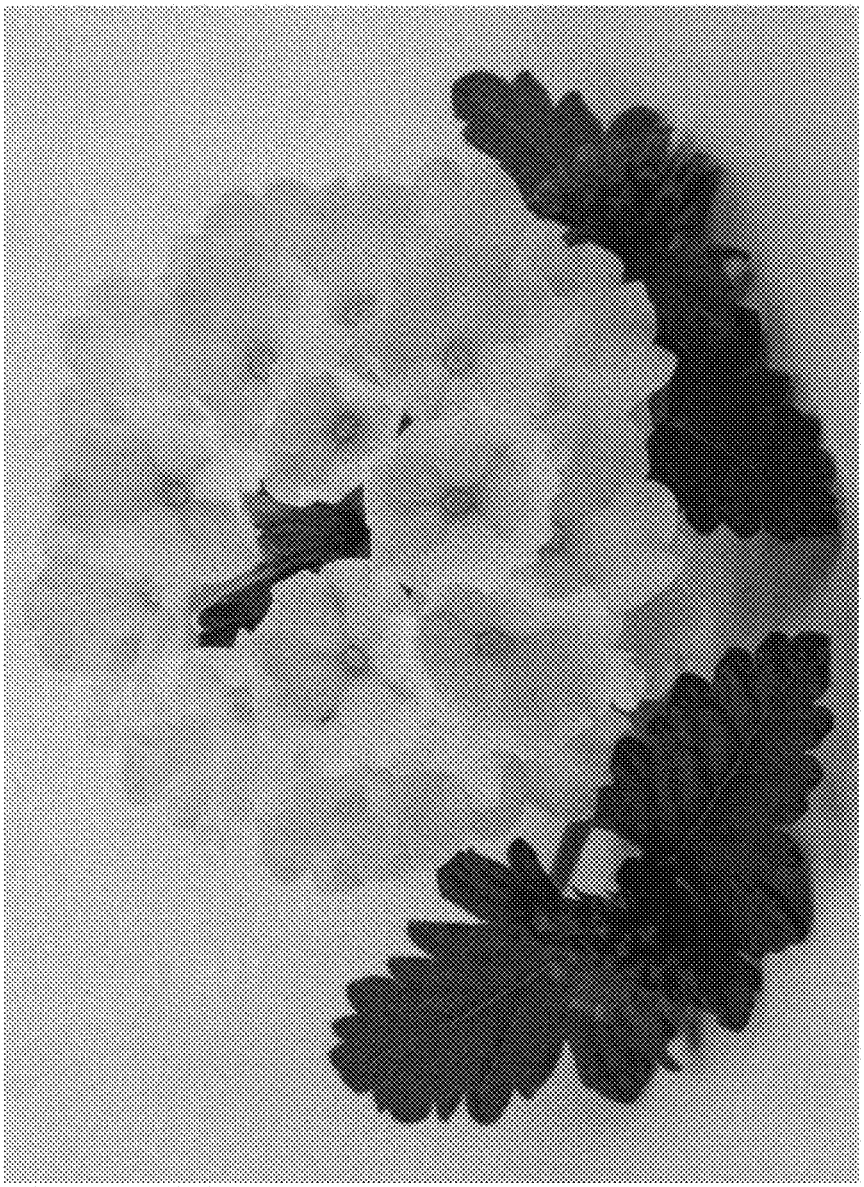

FIG. 2 illustrates in full color a typical inflorescence of 'DVERVNWHI'. Age of the plant photographed is approximately 9 weeks from a rooted cutting in a 12 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DVERVNWHI' plants grown in a nursery in Moshav Mishmar Hashiva, Israel, under natural lighting. Measurements were taken during Autumn of 2018. The plants were approximately 80 days from a rooted cutting in a 12 cm pot. The growing temperature ranged from 18° C. to 27° C. during the days, 10° C. to 15° C. during the nights. Measurements and numerical values represent averages of typical plant types.

Botanical classification: *Verbena hybrida* 'DVERVNWHI'.

PROPAGATION

Time to initiate roots: 7 to 9 days at optimal temperature of approximately 23° C.

Root description: Fibrous. Tan and white, not accurately measured with the R.H.S. chart.

PLANT

Growth habit: Semi-trailing.
Pot size of plant described: 12 cm.
Height: 6 cm.
Plant spread: 40 cm.
Growth rate: Fast.
Branching characteristics: Freely branching.
Length of primary lateral branches: 25 cm.
Diameter of lateral branches: 0.3 cm.
Quantity of primary lateral branches: Approximately 6.
Characteristics of primary lateral branches:
- *Form*.—Cylindrical.
- *Diameter*.—0.3 cm.
- *Color*.—Near Yellow-Green 144A.
- *Texture*.—Pubescent.
- *Strength*.—Flexible.
- *Anthocyanin coloration of stem*.—Absent.

Internode length: 3 cm.

FOLIAGE

Leaf:
- *Arrangement*.—Opposite.
- *Quantity*.—Approximately 20 per branch.
- *Average length*.—4 cm.
- *Average width*.—2 cm.
- *Shape of blade*.—Diamond-shaped. Divided into shallow lobes.
- *Apex*.—Acute.
- *Base*.—Acute.
- *Margin*.—Serrate.
- *Texture both surfaces*.—Pubescent.
- *Pubescence*.—Strigose.
- *Aspect*.—45 degrees.
- *Color*.—Young foliage upper side: Near Green 137D. Young foliage under side: Near Green 138B. Mature foliage upper side: Near Green N137B. Mature foliage under side: Near Green 137D.
- *Venation*.—Type: Pinnate. Venation color upper side: Near Yellow-Green 147C. Venation color under side: Near Yellow-Green 147D.
- *Petiole*.—Length: 1 cm. Diameter: 0.2 cm. Color: Near Yellow-green 144D. Texture: Pubescent.

FLOWER

Natural flowering season: Spring to Autumn under conditions found in Beit Dagan, Israel.
Days to flowering from rooted cutting: 30 to 45 days.
Inflorescence and flower type and habit: Terminal cluster. 4.5-6 cm wide, about 4 cm deep. Broad obovate in profile.
Rate of flower opening: 4 to 6 days from bud to fully opened flower.
Flower longevity on plant: 5 to 8 days.
Persistent or self-cleaning: Self-cleaning.
Bud:
- *Shape*.—Quinquangular.
- *Length*.—1.5 cm.
- *Diameter*.—0.3 cm.
- *Color*.—Near Green 138A.

Corolla:
- *Flower*.—Depth: 1.5 cm. Diameter: 2 cm. Tube. Tube Length: 1.5 cm. Tube Texture: Smooth. Tube opening diameter: 0.1 cm. Petals/lobes: Number: 5. Arrangement: Overlapping. Length: 1.0 cm. Width: 1.0 cm. Shape: Obcordate. Aspect: Upright. Straight along longitudinal axis. Margin: Entire. Texture: Smooth, both surfaces.
- *Color*.—When opening: Upper surface: White NN155B. No eye. Lower surface: White NN155A. Fully opened: Upper surface: White NN155D. No eye. Lower surface: White NN155D. Throat: Color: Yellow-Green 157C. Texture: Smooth. Tube color: Inside: Yellow-Green 157B. Outside: Yellow-Green 157A.

Calyx:
- *Form*.—Tubular.
- *Length*.—1.5 cm.
- *Diameter*.—0.3 cm.
- *Sepal shape*.—Five sepals whose margins are fused-quinquangular.
- *Sepal margin*.—Entire.
- *Sepal texture*.—Pubescent, both surfaces.
- *Sepal color*.—Upper surface: Green 146B. Lower surface: Green 146B.

Pedicels: None.
Fragrance: None.

REPRODUCTIVE ORGANS

Stamens:
- *Number (per flower)*.—4.
- *Filament length*.—0.2 cm.
- *Anthers*.—Shape: Conical. Length: 0.5 cm. Color: Green 145B.

Pollen:

*Color*.—Green-Yellow 1D.

*Amount*.—Few.

Pistils:

*Quantity per flower*.—1.

*Length*.—2 cm.

*Styles*.—Length: 1.2 cm.

*Color*.—Green 145D.

*Stigma*.—Shape: Ovoid. Color: Yellow-Green 143C.

OTHER CHARACTERISTICS

Seeds and fruits: Not observed.

Disease/pest resistance: Tolerant of powdery mildew assumed and unconfirmed pathogens *Podosphaera xanthii* or *Erysiphe cichoracearum*.

Temperature tolerance: Tolerates temperatures from approximately −1° C. to 32° C.

What is claimed is:

1. A new and distinct cultivar of *Verbena* plant named 'DVERVNWHI' as herein illustrated and described.

* * * * *